United States Patent [19]

Eaton, II

[11] 4,265,258

[45] May 5, 1981

[54] DENTAL FLOSS

[76] Inventor: Melvin H. Eaton, II, 2600 W. Landing Rd., Virginia Beach, Va. 23456

[21] Appl. No.: 70,364

[22] Filed: Aug. 28, 1979

[51] Int. Cl.³ .............................................. A61C 15/00
[52] U.S. Cl. ........................................ 132/93; 132/89
[58] Field of Search ................ 132/93, 91, 89, 92 R, 132/92 A

[56] References Cited

U.S. PATENT DOCUMENTS

| | | | |
|---|---|---|---|
| 1,069,874 | 8/1913 | Hanscom | 132/93 |
| 1,149,376 | 8/1915 | Leonard et al. | 132/93 |
| 1,285,988 | 11/1918 | Gudebrod | 132/93 |
| 1,839,486 | 1/1932 | Lawton | 132/93 |
| 1,989,895 | 2/1935 | Gilder | 132/93 |
| 2,381,142 | 8/1945 | Stonehill | 132/89 |
| 2,821,202 | 1/1958 | Davis | 132/93 |
| 3,771,536 | 11/1973 | Dragan | 132/89 |
| 3,789,858 | 2/1974 | Pesce | 132/89 |
| 3,837,351 | 9/1974 | Thornton | 132/89 |
| 3,930,059 | 12/1975 | Wells | 132/93 |
| 4,142,538 | 3/1979 | Thornton | 132/89 |

Primary Examiner—Paul J. Hirsch
Attorney, Agent, or Firm—Beveridge, De Grandi, Kline & Lunsford

[57] ABSTRACT

A new and improved dental floss having a relatively large diameter to provide an increased surface area, and comprised of a multitude of fibers overlaid upon each other such that a number of the fiber ends extend beyond the main body of the dental floss and are somewhat self-supporting. The dental floss has improved cleaning ability and increased shock absorbency which lessens discomfort to the user.

13 Claims, 3 Drawing Figures

DENTAL FLOSS

BACKGROUND OF THE INVENTION

1. Field of the invention

Dental floss is a well-known toilet article used to promote dental hygiene by polishing the surface areas of the teeth and removing unwanted matter from the interproximal areas between the teeth. Typically, in use, a segment of dental floss is passed between the crowns of two adjacent teeth in order to dispose the dental floss in the interproximal space. When the teeth are spaced closely together, the user of dental floss must apply to the ends of the dental floss segment a significant amount of pressure in the direction of the gum. As the dental floss initially passes between the crowns of two closely-spaced teeth, the movement of the dental floss toward the gum is restricted by the two crowns, but as the user continues to work the dental floss past the adjacent crowns, a point is reached at which the teeth are not so closely spaced, and so the movement of the floss toward the gum is suddenly accelerated. When this point is reached, the typical user, and particularly an inexperienced user, is unable to react quickly enough, by releasing the pressure he is exerting, to slow the further movement of the dental floss toward the gum. The result is a sudden movement of the floss, with consequent sudden and forceful contact of the dental floss against the gum, which causes discomfort to the user and often bleeding from the gum. Actual gingival gum injury can result from this forceful action where the tautly stretched, smooth, narrow floss acts in a manner similar to a scalpel. When gingival gum tissue becomes inflamed in an unhealthy state, it swells, turns soft and spongey, and bleeds easily, thus offering less resistance to injury from this cutting effect. Gum disease is at epidemic proportions, and most users of dental floss, whether waxed or unwaxed, smooth or treated, are awkward in its use until they develop the necessary dexterity to prevent this sudden acceleration toward the gum tissue in the interproximal space between the teeth.

2. Description of the prior art

Heretofore, dental floss has been composed of such materials or in such a fashion that the effect of the sudden and forceful contact upon the user's gum has been a problem. The shock-absorbency of prior art dental floss has been insufficient, either due to failure to construct the floss of a shock-absorbing material or due to covering of a potentially shock-absorbing material with a hardened or waxy surface coating.

In addition, many flosses used today are relatively small in diameter, thereby increasing the effect of the forceful striking on a small area of the gum and correspondingly increasing the risk of more intense trauma to that particular area. Of the remaining flosses that have relatively large diameters, the effect of the striking contact is not significantly mitigated, either because alternate portions of the floss have small diameters or because the diameter of the floss is decreased when distended.

In addition to the discomfort caused by heretofore manufactured dental flosses, another disadvantage has been the insufficiency of cleaning capacity caused, at least in part, by the small diameter and the smooth surface of the dental floss. One attempted solution to improve these characteristics has been to manufacture dental floss of a wide, flat ribbon, but such solution has been inadequate due to the difficulty in adequately providing such floss with the preferred textured surface and due to inability to provide such floss with sufficient shock-absorbency. A second attempted solution has been to provide a fibrous floss that possesses an expanded surface area when the floss is not distended, but such solution is likewise inadequate because certain surface areas of the teeth are encrusted with hardened plaque that requires greater floss tension for removal, and when such tension is supplied, this floss becomes distended and its surface area is reduced.

SUMMARY OF THE INVENTION

The present invention is an improved dental floss overcoming these disadvantages of the prior art. Dental floss in accordance with the present invention is formed of a multitude of fibers overlaid upon each other in such a fashion as to allow a number of the fiber ends to extend beyond the main body of the dental floss and to be somewhat self-supporting, thereby increasing the shock absorbency and cleaning ability of the floss. The dental floss of the present invention is further characterized by being compressible or circumferentially deformable and by having a relatively large diameter which provides a greater gum striking area and which is not significantly decreased when a longitudinally distending force is applied to the floss. This dental floss, consequently, engages the teeth with a larger surface area during cleaning and, further, is provided with an uneven surface texture to have an improved abrasive cleaning action, with additional ability of the floss to engage and carry away plaque and food particles. Note that the circumferential diameter is enlarged by the extensions of fibers from the main body of the floss and by the overlapping of fibers, thus increasing the surface area. This dental floss, by virtue of its increased surface area, can clean the interproximal tooth surfaces by lengthwise side-to-side movement as well as by vertical movement against the tooth.

BRIEF DESCRIPTION OF THE DRAWINGS

The description of the present invention will be enhanced by reference to the accompanying drawings in which.

DESCRIPTION OF THE PREFERRED EMBODIMENT

Figure 1:
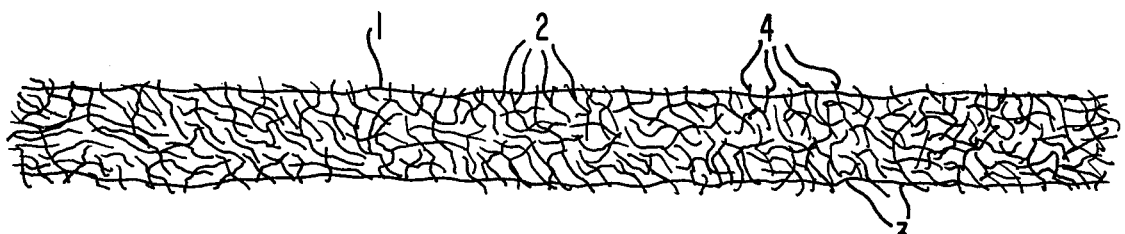
FIG. 1 is an enlarged fragmentary view of dental floss in accordance with the present invention, in the form of a single strand of multitudinous overlaid fibers.

In a first preferred embodiment of the invention, as depicted in FIG. 1, the dental floss is comprised of a single strand 1 of multitudinous overlaid fibers or yarn. Strand 1 is constructed as a multitude of fibers 2 overlaid upon one another. In the preferred embodiment, some of the fibers might be physically joined to each other, while others are merely caught among other fibers. Strand 1 is minimally distensible in its longitudinal dimension and is compressible in its latitudinal dimension. The strand is not covered by a surface coating in order that the individual fiber bodies 3 that comprise the outermost layer of strand 1 are able to come into direct contact with a tooth without being insulated by such surface coating.

The individual fibers that comprise strand 1 do not extend for the length of the strand but instead terminate at different points along the strand. Many of the ends 4 of the fibers are disposed at the surface of the strand. A number of the ends 4 are generally self-supporting and extend beyond the outermost layer of the fiber bodies of strand 1. Preferably, strand 1 is not covered by any surface coating, in order that self-supporting, protruding ends 4 might freely contact adjacent tooth surfaces during use of the floss. The portions of the fiber ends 4 that extend beyond the outermost layer of fiber bodies 3 are long enough to provide additional abrasive cleaning action and additional capacity to attach to and carry away unwanted bacterial plaque and food particles, but are not so long that they become entrapped between the teeth, especially in the process of moving the floss through very small spaces between two teeth.

The diameter of the floss is substantially unaffected by the pulling forces applied to the ends of a segment of the dental floss during use. The diameter of strand 1 is as large as possible while still passing between the crowns of two closely-spaced teeth, but not so large as to present difficulty in such movement. The clearance of the floss as it passes between the crowns of two closely-spaced teeth is accordingly minimal. Typically, the floss body diameter might be in the order of about one-thirty second inch, that is ranging from somewhat less than one-thirty second inch to somewhat greater than one-thirty second inch. Fiber ends 4 typically might extend from the outermost layer of fiber bodies 3 a distance in the order of from about one-sixty fourth inch or somewhat less to about one-sixteenth inch, or somewhat greater, preferably averaging about one-thirty second inch.

Strand 1 may be composed of any synthetic or natural material that will impart qualities to the finished product such that the objectives of the invention may be fulfilled. A preferred material is nylon.

Figure 2:
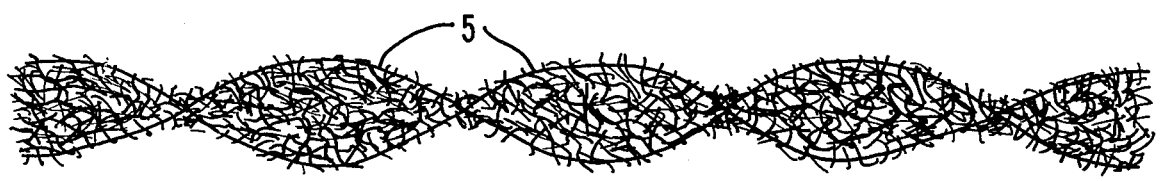
FIG. 2 is an enlarged fragmentary view of a second embodiment of dental floss in accordance with the present invention, in the form of two strands of multitudinous overlaid fibers which strands are wound or twisted about each other.

Improved compression of dental floss in accordance with the present invention might be obtained by forming the floss of more than one strand, thereby easing passage between the closely spaced crowns of two adjacent teeth. Accordingly, as depicted in FIG. 2, a second embodiment of the present invention consists of dental floss having two strands 5 of multitudinous overlaid fibers, each strand having characteristics substantially as set forth above for strand 1 of FIG. 1. The two strands 5 may be knit, wound, or twisted about one another.

Figure 3:
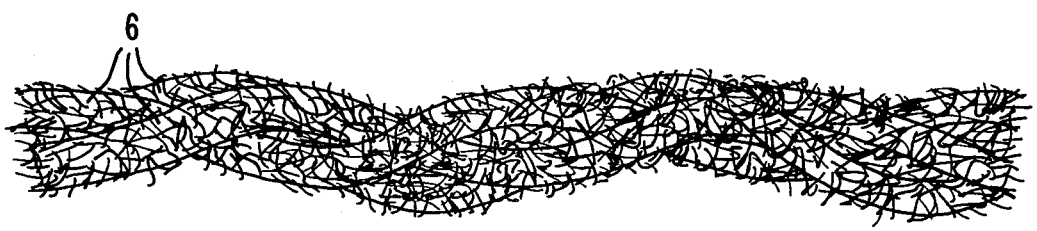
FIG. 3 is an enlarged fragmentary view of a third embodiment of dental floss in accordance with the present invention, in the form of three strands of multitudinous overlaid fibers which strands are wound or twisted about each other.

A third embodiment of dental floss in accordance with the present invention is depicted in FIG. 3 and comprises three strands 6 of multitudinous overlaid fibers, each strand having characteristics substantially as set forth above for strand 1. The three strands 6 may be braided, knit, or otherwise wound or twisted about one another. Additional embodiments might include more than three strands of multitudinous overlaid fibers, in accordance with the present invention.

In the use of the present invention, a segment of the dental floss is caused to pass through the space between two adjacent teeth by exerting a force on the ends of the segment directed toward the gum. Preferably, differential force is applied as the floss segment is shifted alternately between the two sides of the space in such a manner that the force exerted on the tooth on one side is first greater than, then less than the force exerted on the tooth of the other side. This alternating application of force is repeated numerous times to produce a rocking effect that preferably continues until the floss is disposed in the interproximal area. Subsequently, the floss is further carried down to the gingival sulcus, located between the tooth and the tissue. A side-to-side or up-and-down motion is then used to loosen and remove plaque and other material from within the sulcus and from the tooth surface. When the tooth surface and gingival sulcus have been cleaned in this fashion, the floss is then removed, either by pulling the floss completely through the interproximal space, or by causing the floss to pass back out between the crowns of the teeth by means of a rocking force applied in the direction away from the gum. Any loosened matter still remaining between the teeth can then be rinsed away by vigorous swishing action of water or other rinse.

Although the present invention has been described with reference to preferred embodiments, numerous modifications can be made, and still the result will be within the scope of the invention.

What is claimed is:

1. A dental floss comprising a strand of a multitude of fibers overlaid upon each other with a number of the fiber ends extending beyond the outermost layer of fiber bodies, said strand being of substantially uniform diameter, said number of fiber ends extending in random directions, being randomly spaced along the length of said strand, and being substantially self-supporting.

2. A dental floss formed of a plurality of strands as claimed in claim 1.

3. A dental floss as claimed in claim 2 in which the plurality of strands are twisted about each other.

4. A dental floss as claimed in claim 3 formed of two strands.

5. A dental floss as claimed in claim 3 formed of three strands.

6. A dental floss as claimed in claim 2 formed of three strands braided together.

7. A dental floss as claimed in claim 2 in which the plurality of strands are knitted together.

8. A dental floss as claimed in claim 7 formed of two strands.

9. A dental floss as claimed in claim 7 formed of three strands.

10. A dental floss as claimed in claim 1 having a diameter in the order of about one-thirty second inch.

11. A dental floss as claimed in claim 1 in which said fiber ends extend a length in the order of from about one-sixty fourth inch to about one-sixteenth inch beyond the outermost layer of fiber bodies.

12. A dental floss as claimed in claim 11 in which the fiber ends extend a length in the order of about one-thirty second inch beyond the outermost layer of fiber bodies.

13. A dental floss as claimed in claim 1 formed of nylon.

* * * * *